United States Patent
Linder et al.

(10) Patent No.: US 11,974,374 B2
(45) Date of Patent: Apr. 30, 2024

(54) SYSTEMS AND METHODS FOR RETARDING MYOPIA PROGRESSION

(71) Applicant: Reopia Optics, Inc., Danville, CA (US)

(72) Inventors: Barry Jonathan Linder, Danville, CA (US); Yan Zhou, Pleasanton, CA (US)

(73) Assignee: REOPIA OPTICS, INC., Danville, CA (US)

( * ) Notice: Subject to any disclaimer, the term of this patent is extended or adjusted under 35 U.S.C. 154(b) by 179 days.

(21) Appl. No.: 17/246,058

(22) Filed: Apr. 30, 2021

(65) Prior Publication Data
US 2021/0329764 A1 Oct. 21, 2021

Related U.S. Application Data

(63) Continuation-in-part of application No. 16/052,407, filed on Aug. 1, 2018, now Pat. No. 11,000,186.

(60) Provisional application No. 62/540,441, filed on Aug. 2, 2017.

(51) Int. Cl.
*A61N 5/06* (2006.01)
*H05B 47/11* (2020.01)

(52) U.S. Cl.
CPC ........... *H05B 47/11* (2020.01); *A61N 5/0613* (2013.01); *A61N 2005/0626* (2013.01); *A61N 2005/0651* (2013.01); *A61N 2005/0663* (2013.01)

(58) Field of Classification Search
CPC .............................. H05B 47/11; A61N 5/0613
See application file for complete search history.

(56) References Cited

U.S. PATENT DOCUMENTS

| | | |
|---|---|---|
| 2010/0296058 A1 | 11/2010 | Ho et al. |
| 2015/0301670 A1 | 10/2015 | Chiu et al. |
| 2016/0158572 A1 | 6/2016 | Nolan et al. |
| 2018/0345034 A1 | 12/2018 | Butzloff |
| 2019/0038123 A1 | 2/2019 | Linder |
| 2019/0282828 A1 | 9/2019 | Rucker |
| 2020/0089025 A1 | 3/2020 | Li |
| 2020/0409159 A1 | 12/2020 | Samec et al. |
| 2021/0001145 A1 | 1/2021 | Mason |

FOREIGN PATENT DOCUMENTS

| | | |
|---|---|---|
| CN | 203480152 | 3/2014 |
| WO | WO 2017/113824 | 7/2017 |

OTHER PUBLICATIONS

ISA/US, "Notification of Transmittal of the ISR and the Written Opinion of the International Searching Authority, or the Declaration" in PCT Applicatino No. PCT/US2022/026586 dated Jul. 28, 2022, 9 pages.

*Primary Examiner* — Jack Dinh
(74) *Attorney, Agent, or Firm* — Kang S. Lim (57) ABSTRACT

Myopia is a clinically significant and growing problem around the world. A major cause is the increasing time spent indoors by children, for example, playing video games, studying, and watching television. Exposure to sufficient overall light levels is known to be protective, and prevents the onset and also delays the progression of myopia. Embodiments include a computerized myopia progression retarding ("MPR") system that includes a light source configured to provide illumination and an illumination sensor configured to sense ambient light. The MPR system also includes a processor configured to dynamically adjust the illumination in terms of either wavelength bands or luminance provided by the light source to solicit a target wavelength band or luminance for retarding myopia progression of a user.

10 Claims, 8 Drawing Sheets

SYSTEMS AND METHODS FOR RETARDING MYOPIA PROGRESSION

CROSS REFERENCE TO RELATED APPLICATIONS

This non-provisional application is a continuation-in-part and claims priority of U.S. application Ser. No. 16/052,407 of the same title, filed on Aug. 1, 2018, by inventor Barry Linder, recently allowed, which in turn claims priority to U.S. provisional application No. 62/540,441 filed on Aug. 2, 2017, which applications are incorporated herein in their entirety by this reference.

BACKGROUND

The present invention relates to systems and methods for retarding the progression of myopia. More specifically, the invention pertains to use of simulated sunlight to illuminate the eyes to prevent myopia progression.

Myopia is often referred to as near or short sightedness. The incidence of myopia is increasing around the world, with the highest incidence in Asia. The condition is most often diagnosed in early school age children, and in most cases progresses during the subsequent years of school.

There is a growing body of evidence pointing to exposure to outdoor sunlight as a key factor in reducing the incidence of myopic progression in children. Numerous scientific studies have demonstrated the negative association between hours of lower light exposure levels and myopia progression. With increasing education levels, increased socioeconomic levels, and hours of study, the incidence of myopia has been increasing. Furthermore, the length of time spent indoors, e.g., in classrooms, is also increasing.

Currently, there are inadequate interventions that prevent or delay myopic progression. It is therefore apparent that an urgent need exists for effective medical intervention of myopia progression. These improved methods and devices accurately and safely simulate episodic levels of light exposure that children would receive from time outdoors, thereby substantially retarding the progression of myopia, especially in vulnerable K1-12 children.

SUMMARY

To achieve the foregoing and in accordance with the present invention, systems and methods for retarding myopia progression are provided. In particular the systems and methods for simulating sunlight to illuminate the eyes to retard myopia progression in school age children.

A computerized myopia progression retarding ("MPR") system includes a light source configured to provide illumination and an illumination sensor configured to sense ambient light. The MPR system also includes a processor, operatively coupled to the light source and the illumination sensor, configured to dynamically adjust the illumination in terms of either wavelength bands or luminance provided by the light source to solicit a target wavelength band or luminance for retarding myopia progression of a user.

In one embodiment, the MPR system includes a computerized device with a display screen, and wherein the light source of the MPR system is an external ambient light source operatively coupled to the computerized device, thereby enabling the external ambient light source and computerized device to cooperatively provide the target wavelength band or luminance for the user.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "always," "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

Figure 1A:
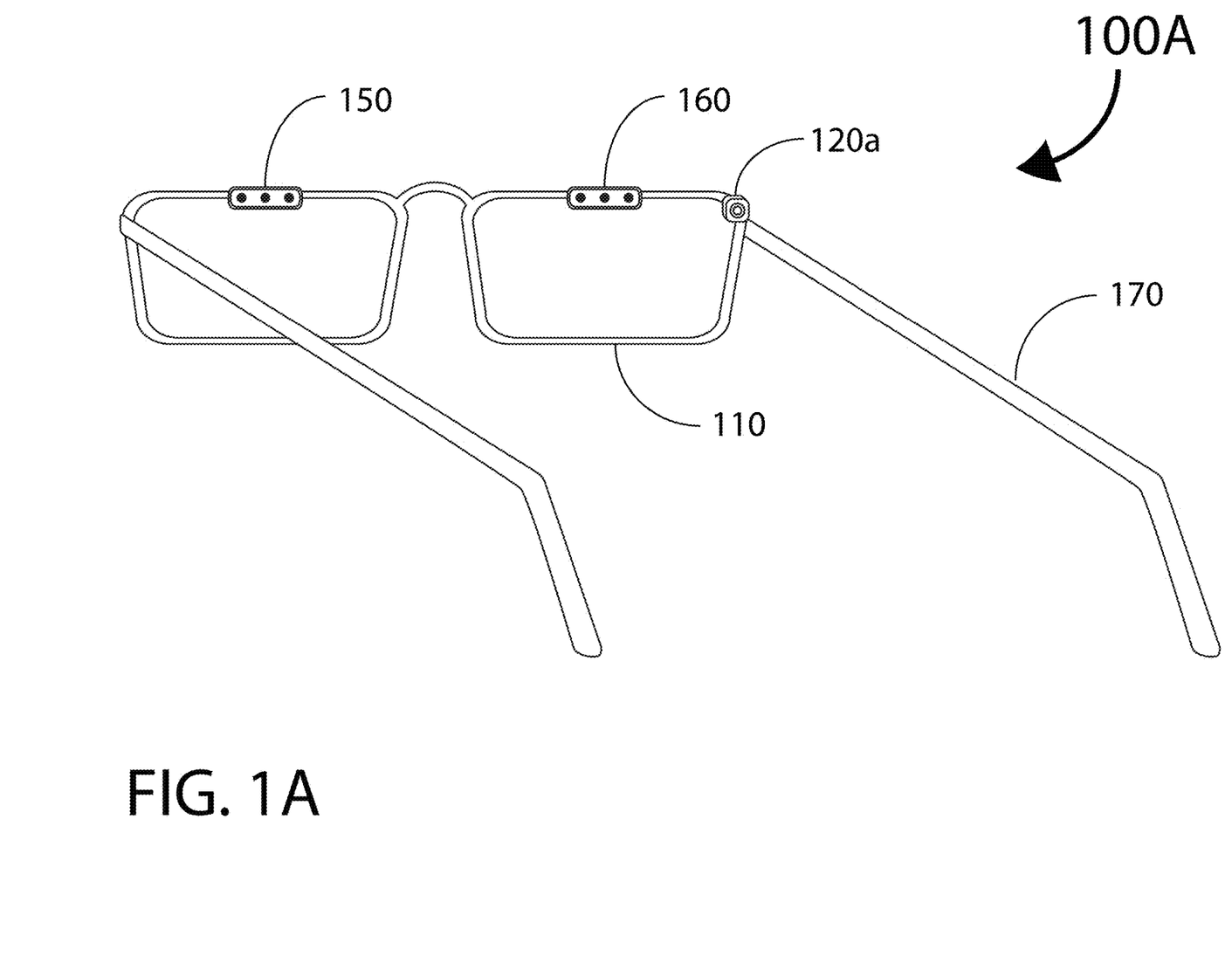
FIGS. 1A and 1B are perspective views of exemplary myopia progression retarders as implemented in eyewear, in accordance with some embodiments of the present invention.
Figure 1B:
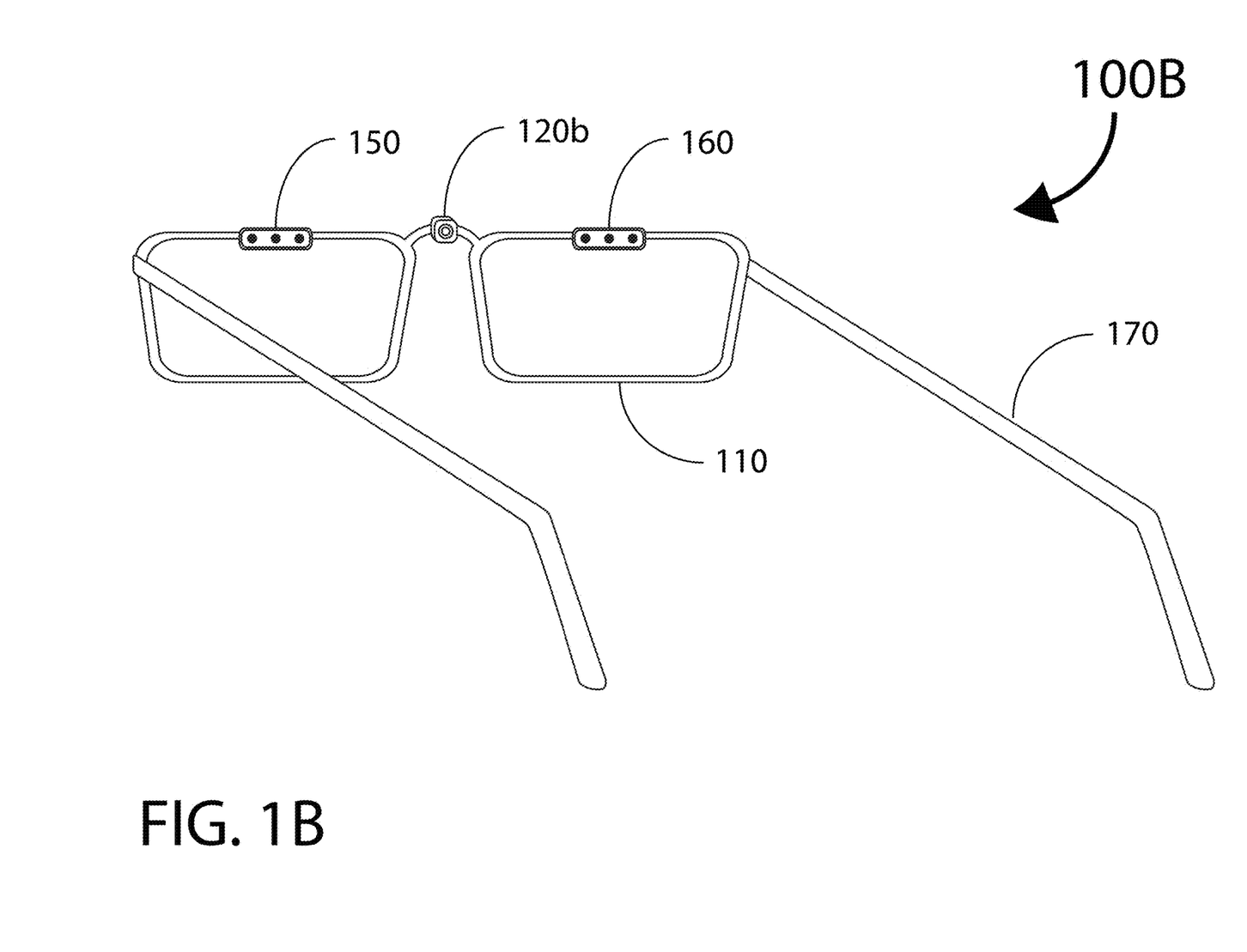

To facilitate discussion, FIGS. 1A and 1B illustrate exemplary embodiments of myopia progression retarders as implemented in eyewear, in accordance with the present invention.

In one embodiment, an eyewear 100A includes a frame 110, a video sensor 120a, and a pair of light sources 150, 160. A microprocessor/microcontroller and an optional transceiver (not shown) can be incorporated into the frame 110 and/or an earpiece 170.

A power source (not shown) can also be incorporated into the frame 110 and/or an earpiece 170. Suitable power sources include rechargeable and/or non-rechargeable batteries. Power can also be generated from head motion via accelerometers. Additional power sources include external wired AC/DC power. Optional supplemental power sources include solar cells. Myopia progression retarders may also be remotely charged via wireless focused-proximity charging and/or inductive charging.

Light sources 150, 160 are configured to simulate the intensity and frequency spectrum of outdoor light, especially sunlight, and can be generated by LEDs or any suitable light sources. Light sources 150, 160 may have adjustable parameters defined by the user and/or third part(ies), for example, a variety of light intensity levels including "Sunny", "direct exposure Sunny" and "in the shade Cloudy", as well as controllable weighting, bandpass, and filtering of wavelengths.

In some embodiments, eyeglass frames include integrated light source(s). The integrated light source can be unilateral or bilateral as illustrated by dual light sources 150, 160. The light source(s) can be a continuous Light Emitting Diode (LED), chosen with wavelengths that simulate the spectrum of natural outdoor light. The LED can have a variable luminance, controlled by the controlling microprocessor, with luminance of approaching 10,000 Lux to simulate the exposure expected outdoors on a typical sunny day.

Users and/or third part(ies) may also be able to control wavelength of illumination delivered to the user by eyewear 100A, such as illuminating with full spectrum of sunlight, variable wavelength(s), visible vs non-visible Bandwidth of chosen wavelength(s), and/or modulate wavelengths during exposure. Choices can also include displaying simultaneously one or more wavelength(s) and bandwidth(s).

In some embodiments, the angle of illumination of the light mounted on a set of frames relative to the entrance pupil of the user's eye can be adjustable. There can be several settings ranging from tangential illumination to nearly perpendicular to the eye's surface.

Video sensor 120a, e.g., a camera, can monitor physiologic pupillary response of the user to the light, thereby enabling the eyewear 100A to ensure adequate light exposure to obtain a target pupillary response. Recording use and compliance of the device is confirmed by active pupillary constriction (i.e. a user cannot simply turn on the light, but eyewear 100A is worn on a live person to obtain a pupillary response).

Video sensor 120a can be sensitive to visible "white" light and/or to other spectra such as infrared light. The purpose of sensor 120a is to monitor the pupillary reaction and size. Since the pupil response to light exposure is bilateral, only one eye's pupil need be monitored. Myopia progression retarders can be calibrated to illuminate the eye with a safe level of luminance that causes a pupillary constriction comparable to natural outdoor light levels. The retarders can work in a closed loop manner such that the controller device maintains the safe level of luminance to maintain the constricted pupil size. Alternatively, the light exposure can be delivered in an open loop manner to utilize a pre-set, non-variable level of light exposure. Further variations in illumination can be programmable, and include as examples alternating on-off-on patterns, as well as simulated illumination levels equal to a sunny day, cloudy day, or sunny day in the shade.

User usage data can be stored locally in eyewear 100A, in a remote server or a combination of both. Eyewear 100A may also be operatively coupled to an application running on a computer, smart phone and/or tablet, via a Bluetooth or WiFi wireless connection.

Usage data collected can include one or all of the following:
1. Duration of exposure
2. Pupillary response
3. Quantitative measure of eye movement
4. Time of day
5. Date
6. Illumination characteristics (wavelength, bandwidth, dynamics, intensity)
7. Head motion from embedded accelerometers
8. Light sensors measuring ambient light
9. Light sensors measuring level of delivered illumination In some embodiments, usage data can be uploaded to existing cloud database(s), such as adding clinical data to patient record, including refraction obtained from physician visits. Correlation to clinical condition can be performed (manually and/or automatically) and illumination recommendations are adjusted as needed to obtain improved clinical outcomes for specific user(s).

FIG. 1B illustrates a modified embodiment of an eyewear 100B which includes a frame 110, a video sensor 120b, and a pair of light sources 150, 160. In this embodiment, the video sensor 120b is located centrally with respect to frame 110.

Figure 2:
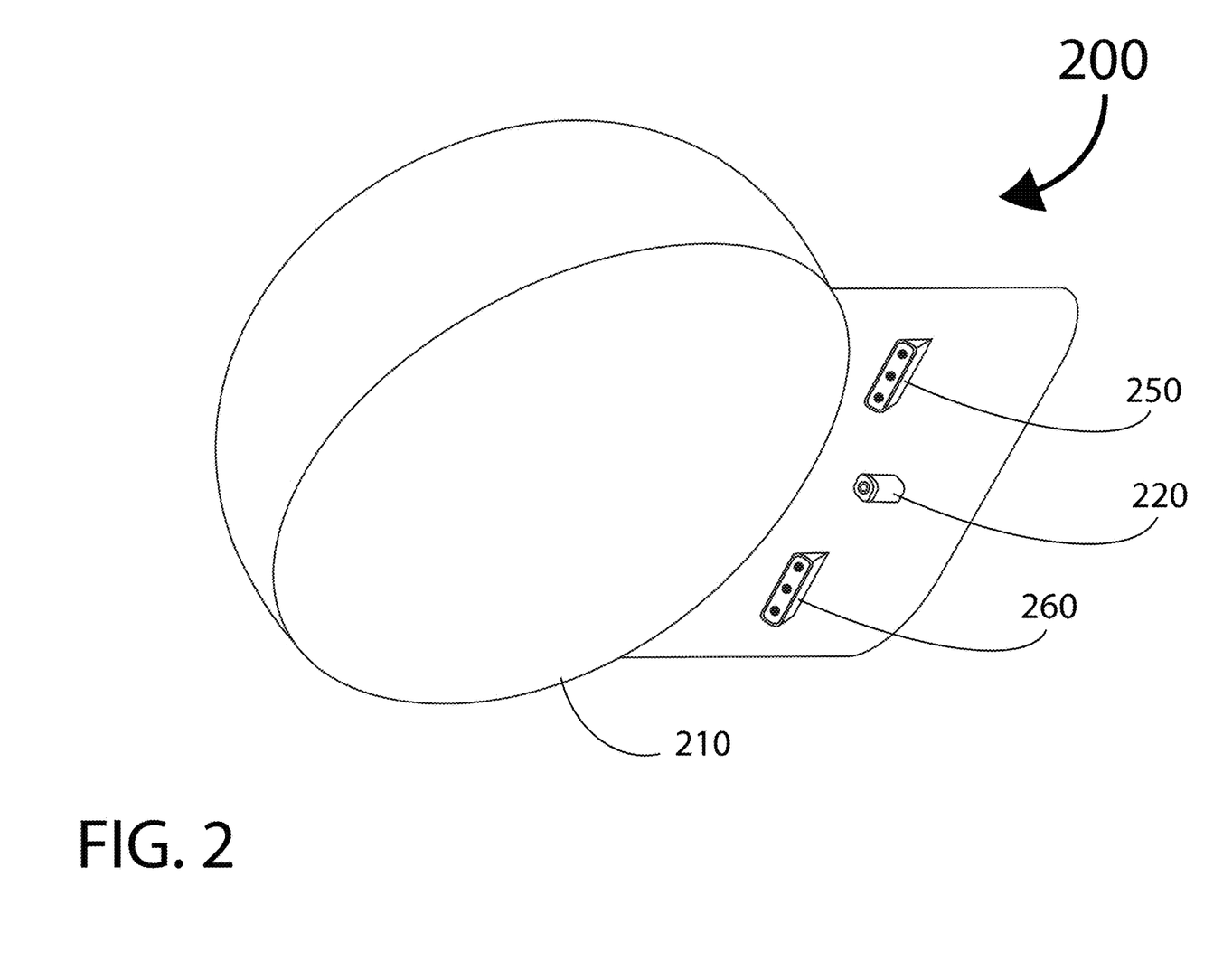
FIG. 2 is a perspective view of a myopia progression retarder as implemented in a headgear, in accordance with another embodiment of the present invention.

As illustrated in FIG. 2, in other embodiments, myopia progression retarders can be implemented in suitable headgear, e.g., a cap 200, having a video sensor 220 and light sources 250, 260. Other exemplary headgear suitable for incorporating myopia progression retarders include hats, visor, hoods and helmets.

It is contemplated that the location and number of light source(s) and camera(s) is not limited to the described embodiments. For example, a single camera can be located toward the center of the eyewear and capable of sensing pupil constriction of both eyes. Similarly, a single light source is located toward the middle of the headgear and provides illumination for both eyes.

For esthetic purposes, it is also possible for the light source(s) to be substantially concealed within the eyewear and the illumination (fiber) optically multiplexed, directed and eventually delivered at each eye through miniature lens. Such an arrangement can advantageously provide a more evenly distributed illumination around the frame and also reduces the weight on the nose piece thereby increasing user comfort and compliance.

In some embodiments, attachments may be added to eyewear or headgear to limit peripheral vision while reading indoors. The attachment can be made from an opaque material to allow ambient lighting to penetrate while blurring out objects otherwise within the user's peripheral field-of-vision.

Figure 3A:
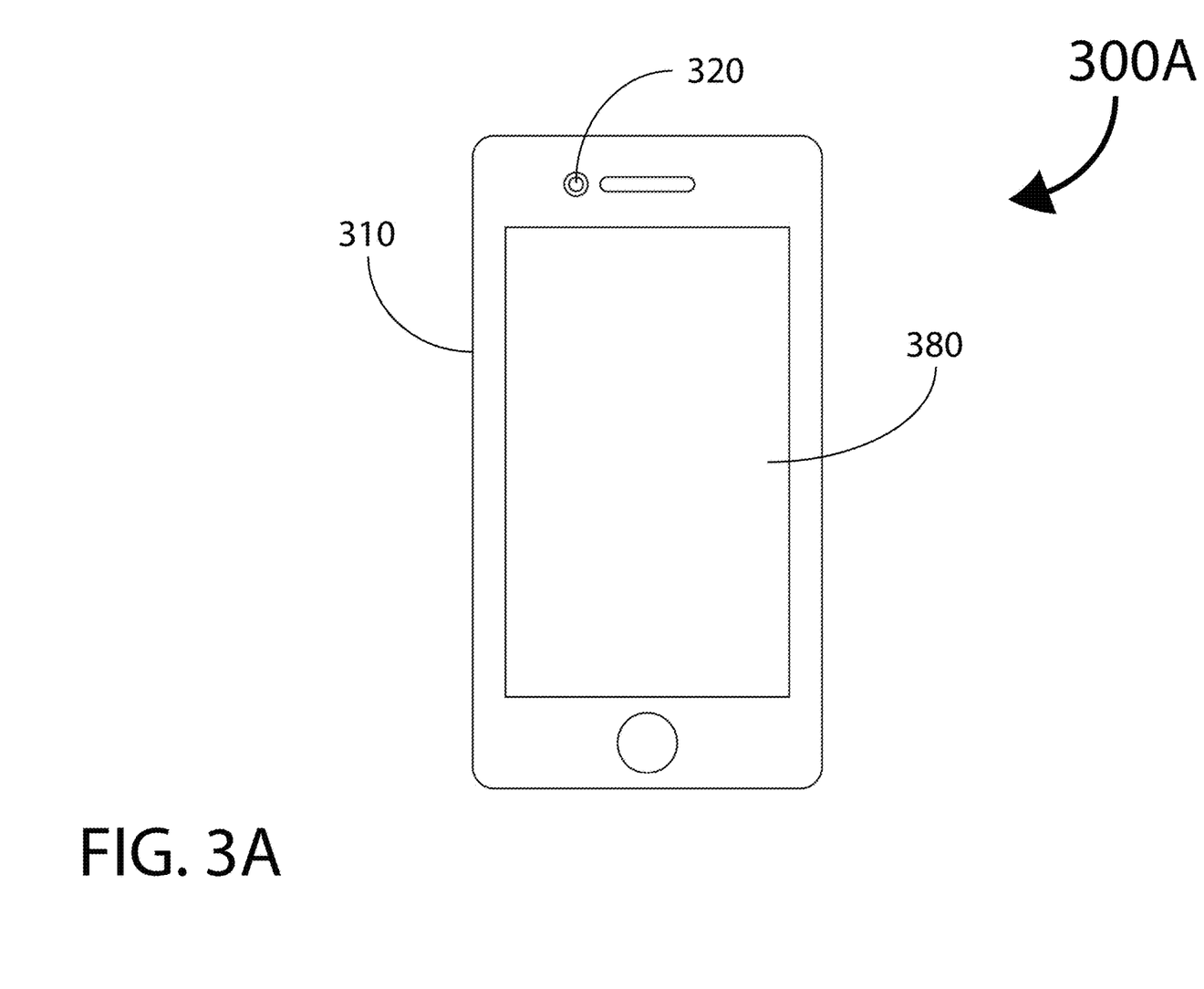
FIG. 3A is a perspective view of a myopia progression retarder as implemented in a smart device, in accordance with yet another embodiment of the present invention.

FIG. 3A depicts yet another embodiment of myopia progression retarder implemented in a computerized device, such as a smart device, a mobile phone, a tablet and a video monitor. In this example, smart phone 300A includes a user-facing camera 320 and a display screen 380 capable of outputting sufficient light intensity and spectrum to simulate sunlight. It is also possible to incorporate myopia progression retarders into Virtual Reality ("VR") or Augmented Reality ("AR") devices, such as VR goggles and AR glasses, to provide the desired level of illumination to the user's eyes.

Figure 4:
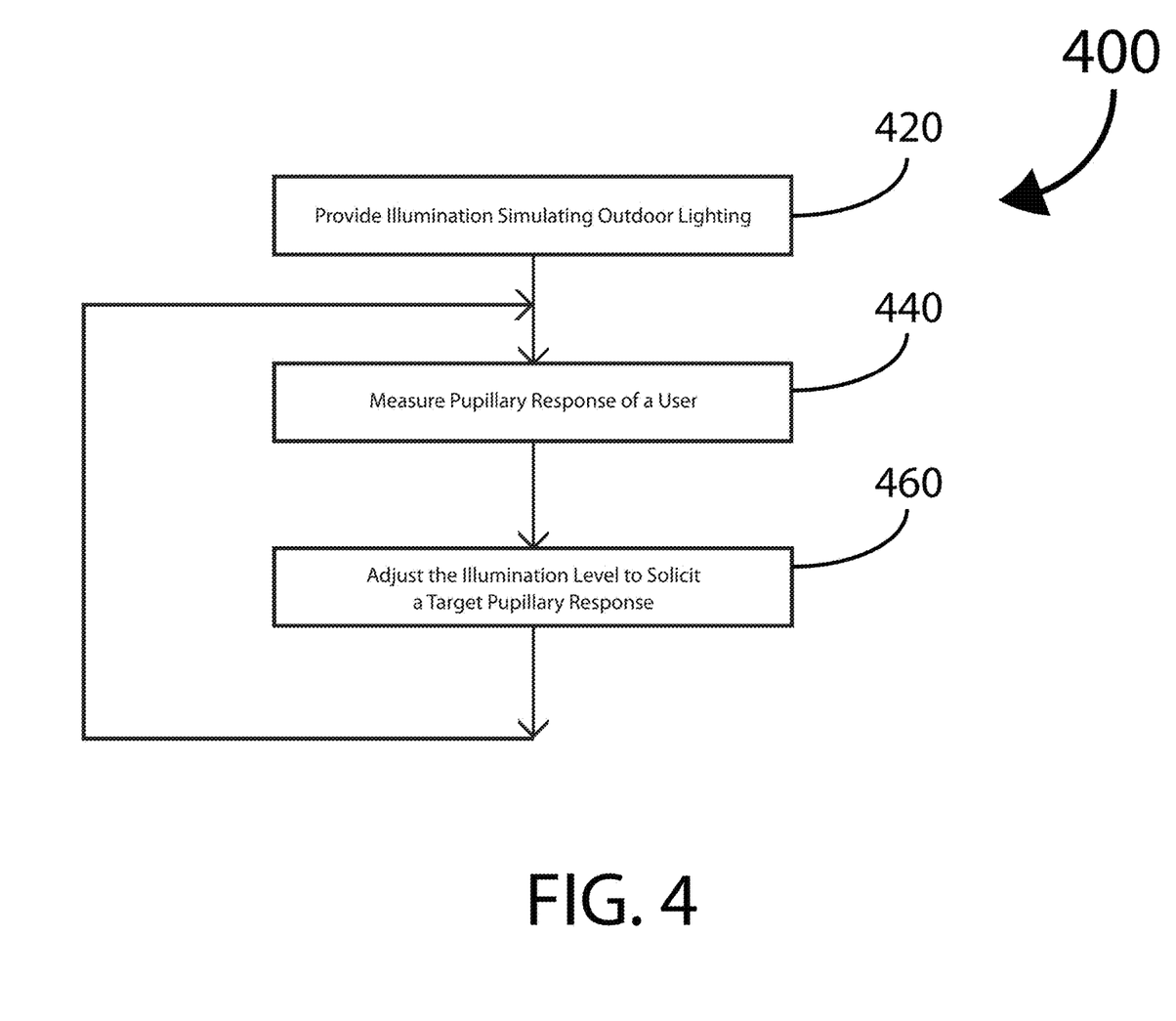
FIG. 4 is a flow diagram illustrating the operation of myopia progression retarders, in accordance with some embodiments of the present invention.

In some embodiments, as illustrated by the flow diagram 400 of FIG. 4, a myopia progression retardation system provides illumination simulating outdoor lighting levels and/or spectrum for a user (step 420). The system measures pupillary response of at least one of the user's eyes (step 440). The system dynamically adjusts the level and/or spectrum of illumination to solicit a desired pupillary response, intended to delay the onset and/or retard the progression of myopia, by maintaining a target pupil constriction consistent with exposure to the outdoor lighting levels and/or spectrum (step 460).

Myopia progression retarders may be capable of communicating with each other and/or a central microprocessor controller in accordance with some embodiments of the present invention. The central controller of such a system can either be a dedicated controller device, or a smart portable device (such as an iPhone) with a software application. The controller can be configurable as a stand-alone device or operatively coupled to a central database via, for example, an internet cloud. Duration of light exposure, illumination level, and pupillary response can be recorded. In addition, a motion detector capable to measuring head movements for eyeglass frame mounted lighting can wirelessly send data to the central database.

Additional optional monitoring sensors can include location, time, integrated metadata including weather, ambient light, and camera to track eye movements, convergent and divergent binocular eye movements, eye targeting movements, and pupillary responses. Real-time automated monitoring of the central data base using artificial intelligence and data mining can also be implemented, and reports routinely generated, or alerts generated if it appears that the lighting system is either not used as recommended, or has been removed from the eyewear or headwear.

Many additional variations and modifications are possible. For example, the light source(s) and camera can be independent components in a kit with universal adaptors to fit each element on any eyeglass frame. Yet another variation of the myopia progression retarder includes the light source without a camera, and the controller works in an open loop manner with pre-set continuous illumination levels.

Alternatively, instead of a video sensor, a solar cell measures the ambient light at the user's location. The myopia progression retarder then computes the amount of supplemental illumination needed to simulate an equivalent outdoor daytime lighting environment.

It is also possible for an external light that simulates light level and spectrum of the outdoor light exposure. This configuration allows the camera and light source to be mounted on stands in a convenient location to the user. A camera can still be utilized to measure pupillary response to ensure sufficient light levels to simulate outdoor exposure. For example, in a classroom setting, a group myopia progression retardation system can include desk-mounted cameras and individualized overhead illumination settings.

Other variants of myopia progression retarders include incorporation of miniature peripheral LED components into a contact lens with peripheral reflective elements to direct light centrally toward the pupil.

Referring again to FIG. 3A, in some embodiments, myopia progression retarding ("MPR") illumination is directly coming from a computerized device 300A, a computer display monitor, a laptop, a cell phone, an augmented reality device or a virtual reality device, having a display screen 380 configured to provide visual content to be displayed to a viewer (not shown). The built-in sensor 320 of device 300A can be configured to also sense ambient light. If the ambient light is missing or lacking certain outdoor spectral band(s) that is(are) particularly effective in prevention myopia or in retarding myopic progression, such as the violet spectral band from 360 nm to 400 nm and/or short wavelength blue light around 480 nm, the MPR illumination provided by display screen 380 can use the ambient sensor signal as an input for adjusting its emission spectral band(s) and/or output level to compensate for the missing spectral band(s), therefore maintaining the presence of the needed spectral band(s) for retarding myopia progression of the viewer.

Figure 3B:
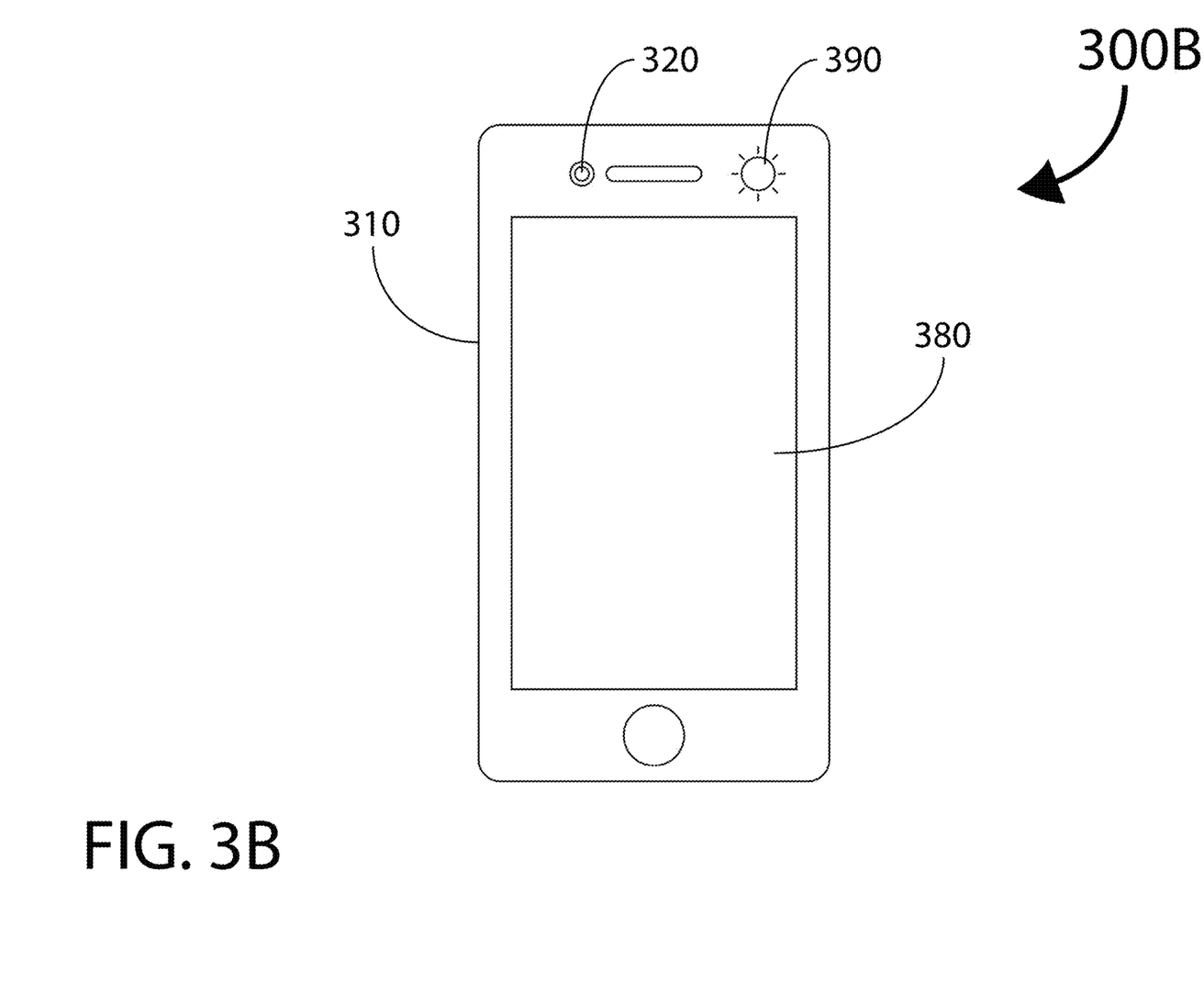
FIG. 3B is a perspective view of another myopia progression retarder as implemented in a smart device, in accordance with yet another embodiment of the present invention.

In another embodiment as illustrated by FIG. 3B, a supplemental illumination source 390 can be incorporated into a computerized myopia progression retarding device 300B, e.g., a computer display monitor, a laptop, a cell phone, an augmented reality device or a virtual reality device, having a display screen 380 configured to provide visual content to be displayed to a viewer (not shown). The built-in sensor 320 of myopia progression retarding device 300B can be configured to also sense ambient light. If the ambient light is missing or lacking certain outdoor spectral band(s) that is(are) particularly effective in prevention myopia or in retarding myopic progression, such as the violet spectral band from 360 nm to 400 nm and/or short wavelength blue light around 480 nm, the supplemental illumination source 390 can use the ambient sensor signal as an input for adjusting its emission spectral band(s) and/or output level to compensate for the missing spectral band(s), therefore maintaining the presence of the needed spectral band(s) for retarding myopia progression of the viewer.

Figure 5:
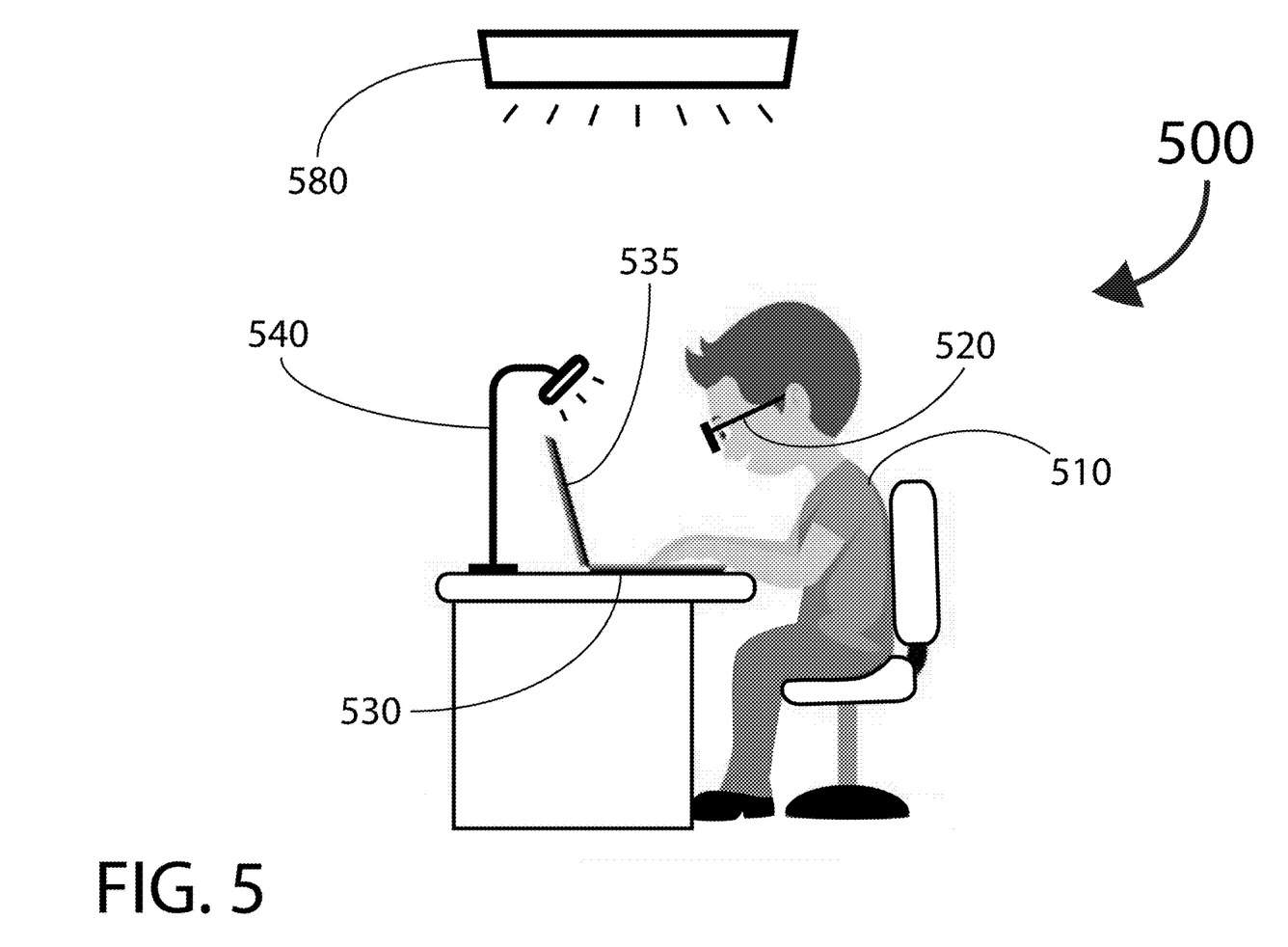
FIG. 5 is a side view depicting yet another embodiment, wherein the illumination sources include not only those coming directly from a computerized device having a display screen providing visual content to be displayed to a viewer, but also those coming from one or more ambient light bulbs or other lighting sources that provide background room lighting.

Referring now to FIG. 5, in yet another embodiment, the illumination sources include not only those coming directly from a computerized device 530, e.g., a computer display monitor, a laptop, a cell phone, an augmented reality device or a virtual reality device, having a display screen 535 configured to provide visual content to be displayed to a viewer 510, but also those coming from one or more ambient light bulbs or other lighting sources that provide background room lighting, such as a table lamp 540 and/or a ceiling light 580. In such an embodiment, the illumination light source coming directly from the display device 530 and the background room light illumination source(s) can be operatively coupled with each other. The myopia progression retarding device 530 can include and/or can be operatively coupled to one or more illumination sensor(s) configured to sense ambient light. Such an exemplary illumination sensor can be incorporated into, for example, a wearable 520. If the ambient light is missing or lacking certain outdoor spectral band(s) that is(are) particularly effective in prevention myopia or in retarding myopic progression, such as the violet spectral band from 360 nm to 400 nm and/or short wavelength blue light around 480 nm, or the indoor lighting luminance level (typically 100-500 lux) is substantially less than that of typical outdoor lighting luminance level ranging from 1000 to over 100 000 lux, the illumination sources, including both that from the display screen 535 and also those that provide background room lighting, can use the ambient sensor signal as an input for adjusting their emission spectral band(s) and/or output luminance level(s) to compensate for the missing spectral band(s) or luminance level, therefore maintaining the presence of the needed spectral band(s) and/or luminance light level for retarding myopia progression of the viewer.

In some variants of the described embodiments, the ambient light sensor(s) can be configured to also sense day/night or light/dark cycle. Based on the continually changing input from the ambient light sensor(s) during the day/night or light/dark cycle, the myopia progression retarding illumination source(s) can change their respective emission spectral band(s) and/or output level to match the natural circadian rhythm, or circadian cycle or normal diurnal cues (e.g., the light/dark cycle) that is related to the ocular rhythms of eye growth and refractive development. For example, when the natural circadian rhythm provided by the ambient light sensor(s) senses the reduction in outdoor light or sunset, signaling the time to not exposing the eye to blue light any more or to dim the illumination light in such a way as to simulate the gradual and symmetrical light—dark transitions at the beginning and end of night, the illumination removes its blue spectral component, and/or emit light at specific spectral band and/or dim light output luminance level to discourage screen time. It may also be possible to substantially maintain the desirable myopia progression retarding illumination levels by increasing longer wavelengths while decreasing blue light.

Figure 6:
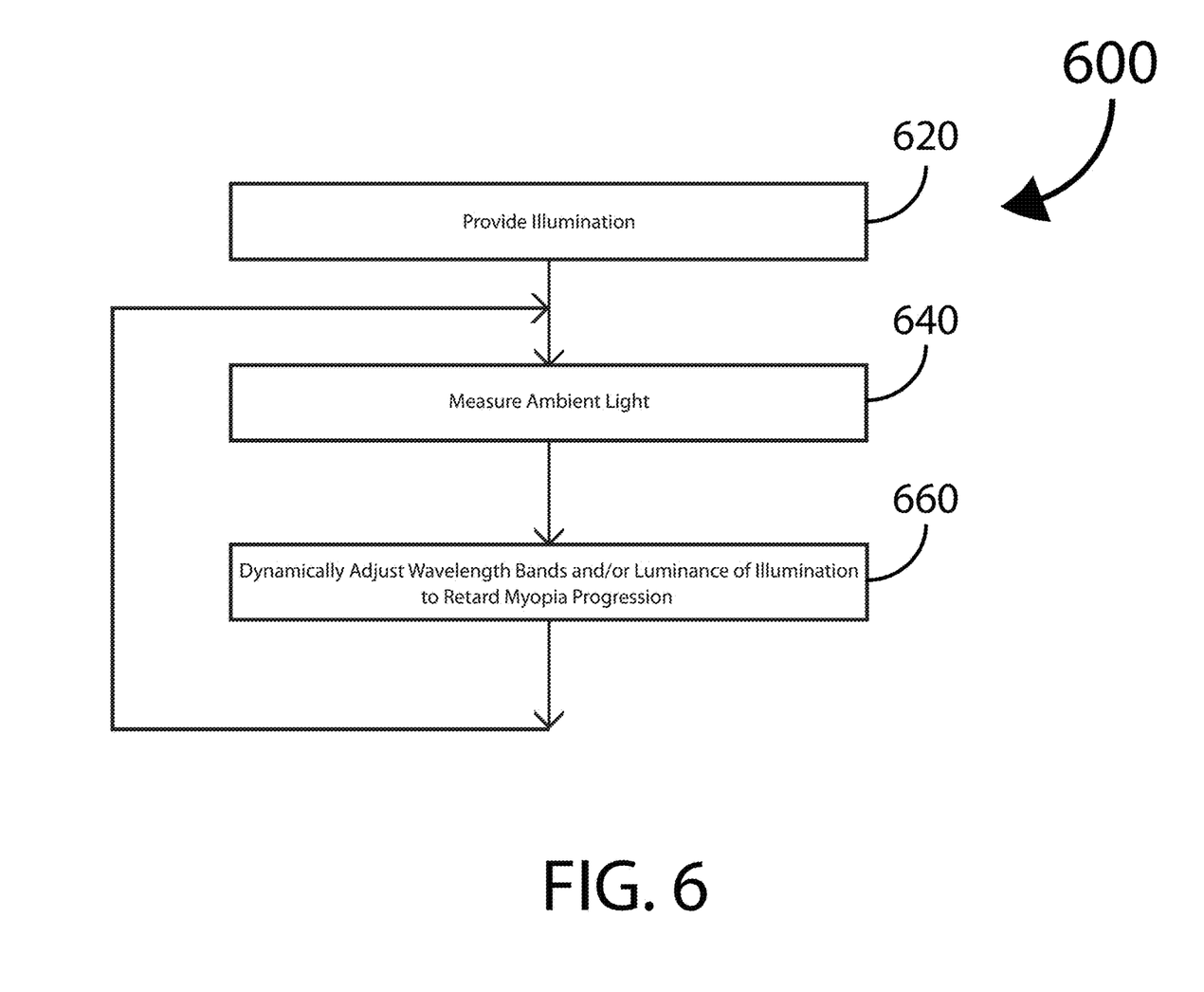
FIG. 6 a flow diagram illustrating the operation of myopia progression retarders, in accordance with other embodiments of the present invention.

FIG. 6 is a flow diagram illustrating the myopia progression retardation methods employed by the various exemplary embodiments of the present invention. In step 620, one or more illumination source(s) can be configured to provide illumination. Ambient sensor(s) are deployed to sense ambient light (see step 640). In step 660, a processor of a computerized device is operatively coupled to the illumination source(s) and the sensor(s). The processor can be configured to dynamically adjust the illumination in terms of either wavelength bands and/or luminance provided by the light source to solicit a target wavelength bands and/or luminance for a user, thereby retarding myopia progression of the viewer.

While this invention has been described in terms of several embodiments, there are alterations, modifications, permutations, and substitute equivalents, which fall within the scope of this invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A computerized myopia progression retarding ("MPR") system comprising:
    a computerized device with a display screen;
    an ambient light source, wherein the computerized device and the ambient light source are configured to cooperatively provide illumination for a user;
    an illumination sensor configured to sense the illumination from both the computerized device and the ambient light source, and
    a processor operatively coupled to the computerized device, the ambient light source and the illumination sensor, wherein based on the illumination sensed by the illumination sensor, the processor is configured to dynamically adjust the illumination in terms of either wavelength bands or luminance provided by the computerized device and the ambient light source to solicit a target wavelength band or luminance for retarding myopia progression of the user.

2. The MPR system of claim 1 further comprising a devise light source incorporated into the computerized device, and wherein the ambient light source, the devise light source, and the display screen cooperatively provide the target wavelength band or luminance for the user.

3. The MPR system of claim 1 wherein the illumination sensor of the MPR system is integrated with a wearable device.

4. The MPR system of claim 1 wherein the computerized device is one of a computer, a smart phone, a tablet and a laptop.

5. The MPR system of claim 1 wherein the MPR system is integrated into a Virtual Reality ("VR") device.

6. The MPR system of claim 1 wherein the MPR system is integrated into an Augmented Reality ("AR") device.

7. A method for retarding myopia progression, the method comprising:
    cooperatively providing a user with illumination from an ambient light source and a computerized device with a display screen;
    using an illumination sensor, sensing illumination from both the ambient light source and the computerized device; and
    based on the sensed illumination, dynamically adjusting the illumination in terms of either wavelength bands or luminance provided by the computerized device and the ambient light source to solicit a target wavelength band or luminance for retarding myopia progression of the user.

8. The method of claim 7 wherein the illumination includes light from a devise light source incorporated into the computerized device, and wherein the ambient light source, the devise light source, and the display screen cooperatively provide the target wavelength band or luminance for the user.

9. The method of claim 7 wherein the illumination sensor is integrated with a wearable device.

10. The method of claim 7 wherein the computerized device is one of a computer, a smart phone, a tablet and a laptop.

* * * * *